(12) United States Patent
Koopman et al.

(10) Patent No.: US 8,846,105 B2
(45) Date of Patent: Sep. 30, 2014

(54) DRY POWDER FIBRIN SEALANT

(75) Inventors: Jacob Koopman, Leiderdorp (NL); Glen Martyn, Melton Mowbray (GB)

(73) Assignee: Profibrix, B.V., Leiden (NL)

( * ) Notice: Subject to any disclaimer, the term of this patent is extended or adjusted under 35 U.S.C. 154(b) by 0 days.

(21) Appl. No.: 13/520,632

(22) PCT Filed: Jan. 7, 2011

(86) PCT No.: PCT/EP2011/050192
§ 371 (c)(1),
(2), (4) Date: Aug. 29, 2012

(87) PCT Pub. No.: WO2011/083154
PCT Pub. Date: Jul. 14, 2011

(65) Prior Publication Data
US 2012/0315305 A1    Dec. 13, 2012

(30) Foreign Application Priority Data
Jan. 8, 2010    (EP) .................................... 10150392

(51) Int. Cl.
*A61K 9/50* (2006.01)
*A61K 38/36* (2006.01)
*A61L 24/10* (2006.01)
*A61K 38/48* (2006.01)
*A61K 9/12* (2006.01)
*A61K 9/16* (2006.01)

(52) U.S. Cl.
CPC ................ *A61K 9/12* (2013.01); *A61K 38/363* (2013.01); *A61L 2400/04* (2013.01); *A61L 24/106* (2013.01); *A61K 38/4833* (2013.01); *A61K 9/16* (2013.01)
USPC ....................................................... 424/499

(58) Field of Classification Search
USPC ....................................................... 424/499
See application file for complete search history.

(56) References Cited

U.S. PATENT DOCUMENTS 6,596,318 B2* 7/2003 Prasch et al. .................. 424/499
2006/0155235 A1* 7/2006 Sawyer ........................... 602/48

FOREIGN PATENT DOCUMENTS

WO    WO97/44015    11/1997
WO    WO99/42146    8/1999

OTHER PUBLICATIONS

International Search Report; International Application No. PCT/EP2011/050192; International Filing Date: Jan. 7, 2011; 3 pages.

* cited by examiner

*Primary Examiner* — Benjamin Packard
(74) *Attorney, Agent, or Firm* — Blank Rome LLP (57) ABSTRACT

The present invention relates to a dry powder fibrin sealant which comprises a mixture of fibrinogen and thrombin for use in surgery, trauma and other wounds or injuries. It further relates to novel formulations comprising said dry powder fibrin sealant for use in the treatment of wounds or for surgical intervention or as a topical hemostat.

15 Claims, 5 Drawing Sheets

DRY POWDER FIBRIN SEALANT

FIELD OF THE INVENTION

This invention relates to a dry powder fibrin sealant, for use in surgery, trauma and other wounds or injuries. It further relates to novel formulations comprising said dry powder fibrin sealant for use in the treatment of wounds or injuries, in particular for use as a topical hemostatic composition.

BACKGROUND OF THE INVENTION

WO97/44015 describes a dry powder fibrin sealant based on micro-particles of fibrinogen and thrombin. Further optimised formulations of these microparticle compositions is described in co-pending non-provisional application U.S. Ser. No. 12/636,718, herein incorporated by reference. In the Examples of this application, the components are prepared by spray-drying, fibrinogen with trehalose and thrombin with trehalose. Each product has a predominant particle size of up to 50 μm in diameter. The fibrin sealant, a blend of these components, has been demonstrated to be an easy-to-use, stable and efficacious topical hemostat. The product can be used immediately, without reconstitution. On contact with aqueous fluid such as blood, the exposed and/or dissolved active thrombin converts the exposed and/or dissolved fibrinogen into insoluble fibrin polymers.

New techniques, devices, and drugs for bleeding and bleeding and/or hemorrhage control are being developed. Despite all of the technology currently available, bleeding and hemorrhage control is still a major unresolved problem in emergency medical care. Almost 50% of all deaths in the first 48 hours of hospitalization are related to an inability to adequately control bleeding. Failure to stop bleeding within the first 24 hours is almost always fatal, especially when multiple trauma sites are involved.

It is generally accepted that hemostatic products for forward care in a battle zone must control bleeding quickly, be ready to use, simple to apply, have a shelf life approaching two years and prevent bacterial or viral transmission. The product's hemostatic action is time-critical in order to meet both military and civilian needs. Devices being investigated or used today as external methods of wound treatment range from absorbent pads containing clotting agents, pressure bandages, gauze, tourniquets for extremities, and trauma kits for wounds to the body.

Agents designed to stop external bleeding differ in composition and components are designed to help the rapid formation of a clot at the site of application. Clotting products generally contain high concentrations of materials such as human fibrinogen, thrombin, calcium, factor XIII and/or anti-fibrinolytics. In addition to fibrin, microporous polysaccharide macrobeads, mineral and synthetic zeolites, and chitosan (poly-N-acetyl glucosamine) are also available for use as hemostats. A number of new hemostatic products are available for treating wound trauma, for example, a bandage product using chitosan (deacetylated poly-N-acetyl glucosamine base, HemCon Inc., Tigard, Oreg.). However, it only has a shelf life of 18 months and its cost is prohibitive. Z-Medica Corporation, Wallingford, Conn., market a pressure bandage product (QuikClot) for use by U.S. troops. This product uses a granular, synthetic mineral zeolite to stop bleeding by adsorbing liquid and promoting clotting. However, QuikClot generates heat that can cause burns if the bandage isn't applied correctly.

ActSys Medical Inc., Westlake Village, Calif., provides a hemostatic gauze product, ActCel, which is a collagen-like natural substance created from chemically treated cellulose. It expands 3-4 times its original size when in contact with blood, thus sealing off damaged vessels and aiding clotting.

Medafor Inc., Minneapolis, Minn., sell a bio-inert, microporous polysaccharide macrobead product that is synthesized from potatoes, called TraumaDEX. This powdered microporous polymer product stops bleeding by expanding at the wound site and dehydrating the blood, whereupon the body absorbs the material within 48 hours.

Another non-bandage approach employs a non-zeolite topical powder containing a hydrophilic polymer and potassium salt (Quick Relief, Sarasota, Fla.) which, after application produces a flexible, protective scab to cover the wound site when the powder contacts the blood and slight pressure is applied.

No perfect solution currently exists for the treatment of excessive bleeding. Heat generation with respect to one type of agent is a major problem. The dressing's ability to adhere effectively when applied to deep wounds or wounds of irregular shape creates another major limitation. The ability to deal with excessive blood is another drawback, as is treatment and control of pressure bleeding from arterial bleeding.

Surgical and trauma wounds are the most common types of wounds addressed in the wound-care arena. Current bandages are made of gauze and are often applied in conjunction with an elastic bandage. They allow the wound to breath but are poor barriers to subsequent contamination. These bandages cannot stop serious bleeding and require the application of pressure in the case of arterial bleeding. Conventional wound sealants fail to present an optimized combination of speed of clotting, effectiveness under pressure bleeding conditions, and clots that are dynamic over time in response to the needs of the trauma site. Typical wound sealants are usually used in conjunction with separate wound dressings. Clearly, surgical trauma caused by sharp objects occurs in a clean environment. However, trauma wounds not caused in a controlled environment are often intermediate sized, widespread, and dirty wounds with considerable tissue damage are found in road traffic accidents or on the battlefield.

Abrasions are generally caused by scraping of the skin's outer layer; lacerations are jagged, irregular cuts or tears of the skin; punctures are caused by an object piercing the skin layers, creating a small hole; incisions are cuts commonly caused by knives or other sharp objects; and burns cause damage which may vary greatly in depth, size, and severity. Wounds due to firearms can be deep and with substantial tissue destruction. Dismemberment due to trauma requires immediate intervention to stop blood loss from the severed limb.

Liquid bandage formulations are available to the Over-the-Counter (OTC) consumer market. Liquid bandage preparations are often used for covering and protecting minor lacerations and abrasions, friction blisters and paper cuts. When applied to the skin, the solution evaporates to form a protective film over the application area and to promote healing. The polymerized film covering creates a moist wound healing environment to increase wound healing compared with conventional dressings. Most liquid bandage preparations claim to stop minor bleeding, create a protective seal over the wound, and keep out water, dirt and germs. These preparations generally act as a mechanical barrier to common microbial organisms and other forms of contamination. Liquid bandage products are available from numerous commercial sources and include New Skin Liquid Bandage, Nexcare Bandages Spray Liquid Bandage, Liquid Bandage by J&J, Skin Shield Liquid Bandage Curad Spray Bandage. Powder-based hemostats are also widely available OTC in products such as QuikClot (Z-Medica), Urgent QR and Nosebleed QR (BI-OLIFE), TraumaDEX and Bleed-X (Medafor), Celox (MEDTRADE Biopolymers), ActCel (ActSys Medical), and Quick Relief.

Publication WO 96/17633 describes tissue sealants including a fibrin bandage. In the method used for generating the bandage described in the WO publication, the active components are lyophilized in separate layers which are supported by an occlusive backing. Therefore, the active components are not homogeneously mixed throughout the bandage.

EP 1073485 (Zymogenetics) describes fully recombinant tissue sealant compositions, but makes no reference to dry powder forms.

SUMMARY OF THE INVENTION

A fibrin sealant according to the present invention is of the general type described in WO97/44105, and further optimised formulations of these microparticle compositions is described in co-pending application U.S. Ser. No. 12/636,718, herein incorporated by reference. These microparticle blends may optionally additionally comprise a biocompatible, water-absorbent, water-swellable additive material, or a water-soluble additive material or a biocompatible, water-absorbent, silica additive material. The additive material can act as a carrier or diluent, may enhance powder flow and wettability and also may have the effect of increasing absorbance of fluid of the bleeding wound, thereby decreasing the local tissue fluid and hence increasing the relative concentration of clotting factors in the wound. By this, the effectiveness of the fibrin sealant is increased. The invention also provides a fibrin sealant product that has efficacy at low fibrinogen levels.

BRIEF DESCRIPTION OF THE FIGURES

FIG. 1 Liver scallop injury model. 1A shows the injury that is made; 1B shows the Sephadex-blended Fibrocaps™ being applied and 1C shows the Vicryl sheet covering the powder after 30 sec of pressure with gauze.

DETAILED DESCRIPTION

The compositions of the invention can meet the primary objectives of achieving good flow properties, enhanced wettability and enhanced, effective delivery to the active site, and dissolution only at the site, not in the delivery system.

The fibrinogen and the thrombin may be isolated from blood from human donors or, more preferably, be made by recombinant DNA technology in cultured cells or transgenic animals or plants.

The fibrinogen or thrombin may be full-length, wild-type (625 or 621 amino acids for fibrinogen) or any active fragment thereof. Fragments are known; see Coller et al, J. Clin. Invest. 89:546-555 (1992). Also variants forms may be used. Particularly suitable variant forms of fibrinogen include variants which are the result of alternative splicing, such as the so-called gamma prime ($\gamma'$ variant) and the $\alpha$-ext Fib or Fib420 variant. Fibrinogen raw material may be a frozen solution, although, lyophilised powder which requires reconstitution prior to spray-drying may be used.

The content of fibrinogen in the microparticles containing it may be about 0.1 to 50% w/w, preferably about 0.5 to 20% w/w, as well as 5 to 10% w/w, or about 6.5% w/w. The content of thrombin in the microparticles containing it may be about 10 to 20,000 IU/g, preferably about 25 to 1000 IU/g, or 100 to 500 IU/g, or about 270 IU/g.

The active-containing microparticles and/or additive material may be solid or hollow, such as in the case of microcapsules. Microparticles comprising fibrinogen or thrombin may be prepared by methods known in the art, for example as described in WO 92/18164, WO 96/09814, WO 96/18388 or WO 97/44015. These spray-drying and associated particle manipulation processes enable the production of soluble protein microcapsules with defined size distribution, for example of up to 50 micrometer in diameter. For example, as described in those documents, the microparticles may be produced reproducibly, e.g. with 90% or more (by volume) up to 30 µm, e.g. 10 to 20 µm, in size. Readily-flowing agglomerates of these particles may be made in situ by adjusting the air flow configuration in the spray-dryer to counter-current, or arranging multiple atomisers into a "forced primary agglomeration" set-up, as would be appreciated by persons skilled in the art. Such agglomerates may be 50 to 1000 microns or 100 to 500 microns, or 125 to 250 microns in diameter. Respective fibrinogen-containing and thrombin-containing soluble microparticles can be formulated and blended together within a spray-drying apparatus by the use of a multi-nozzle atomizer, as described in WO03/037303.

Although the preferred method of preparation of the dry powder formulation includes spray drying, other drying techniques may also be used to prepare the dry powder formulation. Suitable methods are known in the art and include fluidized bed drying and freeze-drying, with subsequent micronisation, or via spray-freeze drying. Microparticles may be sterilised, if necessary or desired, using techniques known in the art.

Microparticles of the invention are preferably prepared by spray-drying. Typically, a 2-fluid nozzle is used which utilises compressed air during the atomisation process; this results in the production of hollow microparticles. The maximum particle size of microparticles (X50, as measured by Sympatec) that can be manufactured using this atomisation system on the Niro Mobile Minor spray dryer is ~30 µm. Preferred X50 values for the micoparticles of the invention are between 5 and 50 microns, most preferably between 10 and 20 microns.

The solid or hollow fibrinogen-containing microparticles are then blended first, with the solid or hollow thrombin-containing microparticles and optionally then the additive material as described herein, vice versa, or in any sequence which produces a homogenous blend. Such blending can be carried out using low shear or high-shear blending, or any other technique known to persons skilled in the art.

Microparticles of the invention may be prepared by spray-drying a solution of the active component with a saccharide alone, such as mono- and di-saccharides, including lactose, mannitol and trehalose, or poysaccharides such as dextran. An alternative procedure comprises co-spray-drying, in which fibrinogen or thrombin and another wall-forming material are formulated and spray-dried, to give microparticles in which the active component is incorporated into the particle.

Suitable other proteins may be naturally occurring or be made by recombinant DNA technology in cultured cells or transgenic animals or plants. They may act as "wall-forming materials", as described in WO92/18164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and trehalose. Other suitable substitutes for HSA include surfactants, such as Tween 20, Tween 80, Poloxamer 407 or Poloxamer 188. Calcium ion, e.g. as calcium chloride, may be incorporated in the thrombin feedstock. Alternatively, calcium chloride may be added to the microparticles after processing.

In an embodiment of the invention, an additive material may also be present. The additive material used in the invention typically has a particle size of 10 nm to 1 mm or about 10 microns to 1000 μm. Where the additive is chosen to act as a carrier, the particle size may be between 10 to 1000 μm, or 100 to 500 μm, or 125 to 250 μm or possibly e.g. 10 to 40 μm. They may comprise one material or a mixture.

The additive material may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, by weight of the composition, or any range between.

Various materials are suitable for use as the biocompatible, water-absorbent, water-swellable additive material, for enhancing flow and wettability, etc. Preferably the material is insoluble or very slowly soluble. Such materials may include dextran polymers, like e.g. Sephadex, which are available in different particle sizes, starches, pullulan derivatives, hyaluronic acid esters, cellulose products such as microcrystalline cellulose (Avicel range), methylcellulose, carboxymethyl cellulose, microfine cellulose or hydroxy propyl cellulose, hydroxypropylmethylcellulose, hydroxypropylcellulose, low-substituted hydroxypropyl cellulose, hydroxyethylcellulose and other materials such as cross-linked polyvinyl pyrrolidone (PVP), may be used singly or in admixture. Also, suitable additive materials acting as carriers include polyethylene glycol (PEG), preferably having a molecular weight of about 1000; polyvinylpyrrolidone (PVP), preferably having an average molecular weight of about 50,000; Poly(acrylic acid), polyacrylamide, poly vinyl alcohol (PVA), Poly(methylvinylether co-maleic anhydride), Poly(ethyleneoxide), and dextran, typically having an average molecular weight of about 40,000. Microparticles of the invention may be sterilised, if necessary or desired. Sterile processing, electron beam irradiation, γ-irradiation and ethylene oxide are examples of suitable techniques.

The additional particles used in the invention (described herein as "carrier particles") typically have a particle size of 10 to 1000 μm, e.g. 10 to 40 μm. They may comprise one material or a mixture.

Various materials are suitable for the large carrier materials for fibrin sealant, for enhancing flow and wettability, etc. They include saccharides such as mono- and di-saccharides, including lactose, mannitol and trehalose, or dextran and dextran polymers, like e.g. Sephadex, which are available in different particle sizes.

Cellulose products such as microcrystalline cellulose (Avicel range), methylcellulose, carboxymethyl cellulose, microfine cellulose or hydroxy propyl cellulose, and other materials such as cross-linked polyvinyl pyrrolidone (PVP), used singly or in admixture. Also, suitable carriers include include polyethylene glycol (PEG), preferably having a molecular weight of about 1000; polyvinylpyrrolidone (PVP), preferably having an average molecular weight of about 50,000; Poly(acrylic acid), PVA, Poly(methylvinylether co-maleic anhydride), Poly(ethyleneoxide), and dextran, typically having an average molecular weight of about 40,000.

Tablet disintegrants may be included. These materials will absorb moisture from the wound, expand rapidly and thereby enhance the wettability of the hemostatic components of the powder blend:

Sodium starch glycolate (Explotab or Primojel)—has an average particle size in the range of 35-55 μm. About 25% of the glucose units are carboxymethylated.
cross-linked polyvinyl pyrrolidone (polyplasdone)
alginates and alginic acid
cross-linked sodium carboxymethylcellulose (Ac-Di-Sol)

Gums and gelling agents that can be used include, for example, Tragacanth, Karaya gum, soluble starch, Gelatin, Pectin, Guar gum and Gellan gum. A particularly preferred additive is Emdex, i.e. a hydrated form of dextrates (spray crystallized dextrose containing small amounts of starch oligosaccharides). It is a highly refined product composed of white, free-flowing, spray-crystallized macroporous spheres with a median particle size of 190-220 μm.

Another preferred additive is NON-PAREIL SEEDS®: (Sugar Spheres). These are used in multiple drug units for improved content uniformity, consistent and controlled drug release and high drug stability, size ranges from 200 to 2000 mm.

A most preferred carrier additive is sorbitol or mannitol in the highly porous and highly soluble interwoven filamentary crystal form as sold under the name PARTECK SI and PARTECK M (Merck KGaA, Darmstadt, Germany). These grades have a high adsorption capacity and so are suitable for blending with the dry powder fibrin sealant powder composition of the invention, to produce a novel powder which reduces dusting, enhances wettability, solubilisation and performance of the dry powder fibrin sealant, by allowing blood to soak through the applied powder bed and thus avoid clotting at the powder interface alone.

In another embodiment of the invention, the carrier particles may comprise an effervescent couple. The gas produced following an effervescent reaction can expand the fibrin sealant into a 'foam' and/or increase wettability of the powders comprising the fibrin sealant. As the powders are applied to a wound, the effervescent components dissolve, react and liberate, say, carbon dioxide, thereby increasing the wettability of the hemostatic components and thus enhancing time to clot formation. The fibrin sealant will appear as a stable foam once fully reacted and the clot has formed.

The effervescent couple typically comprises citric acid or sodium hydrogen citrate and sodium bicarbonate, but other physiologically acceptable acid/alkaline or alkaline earth metal carbonate mixtures may be used, for example tartaric, adipic, fumaric or malic acids, and sodium, potassium or calcium (bi)carbonates or sodium glycine carbonate. In general it has been found that preferred taste characteristics are exhibited when the relative proportions of the components of the effervescent couple on a chemical molecular equivalent basis are in the range of 4:3 to 1:3, more preferably about 2:3, expressed as the ratio of molecular equivalent of the acidic component to the basic component. In terms of a preferred combination of citric acid and sodium bicarbonate these values represent on a weight basis, a range from 1:1 to 0.3:1, preferably 0.5:1 expressed as the ratio of acidic to basic component.

Another preferred additive material is a silica, preferably those that are hydrophilic. Such silicas may be colloidal silicas, fumed silicas, ground silicas, precipitated silicas, or mixtures thereof. Examples of suitable fumed silicas include but are not limited to, Aerosil® 90, 130, 150, 200, 300, 380, R202, R805, R812, R972, R974 (Degussa Corporation, Ridgefield Park, N.J.) and CAB-0-SIL.® TS-720 and M-5 (Cabot Corporation, Tuscola, Ill.). Generally, Aerosil.®. 200, Aerosil.®. R974, CAB-O-SIL.®. TS-720 and any other generally equivalent products from other manufacturers of fumed silicas are preferred. It is known that hydrophilic AEROSIL® colloidal silica increases the rate of tablet disintegration and active ingredient release. The colloidal silica acts as a "wick" to draw the water—for example from the digestive juices—into the interior of the tablet. Moreover, tablet ingredients "coated" with hydrophilic AEROSIL® 200 colloidal silica are more easily wetted and swell faster (disintegrants) or dissolve faster (active ingredient). Such properties enhance the wettability and dissolution of the powdered fibrin sealant of the instant invention. Furthermore, such silicas are known to act as glidants, and so will enhance the flowability, filling and delivery of such cohesive microparticulates. Moreover, such colloidal silicas are known activators for blood clotting and thus act synergistically with the fibrinogen and thrombin components (see Margolis, "The Effect of Colloidal Silica on Blood Coagulation", Aust. J. Exp. Biol., 39, pp. 249-258 (1961)). The composition may comprise between 0.001 to 5% w/w, or about 0.01 to 2% or about 0.1 to 0.5% w/w of a silica. The silica may be simply blended with the fibrinogen-containing component and then the thrombin-containing component added thereto and blended further, or vice versa. Most preferably the silica is blended with the pre-blended powdered components as a final step. Suitable blending apparatus will be known to those skilled in the art, the silica may be present in combination with a carrier additive particle, as defined herein.

The additive material may be present in the composition of the invention as single components or in combination and may be present in the feedstock or added to either the spray-dried thrombin or fibrinogen component before blending together, or added to the final blend and subjected to further blending. Such blending can be carried out using low shear or high-shear blending, mechano-chemical bonding, hybridisation or any other technique known to persons skilled in the art.

Although the components of the microparticles in a fibrin sealant of the invention are preferably water-soluble, and the microparticles are preferably obtained by spray-drying a suitable solution, the microparticles that are obtainable may be free-flowing, discrete and substantially dry or anhydrous, with a residual moisture content preferably no greater than 8% w/w, most preferably no greater than 5 or 3% w/w. This means that the compounds of fibrin sealant in accordance with this invention are not activated until they are wetted, e.g. by coming into contact with liquid at a wound site. The active components may therefore be delivered as a dry mixture, although separate application of the different microparticles is also envisaged. The active-containing microparticles are preferably amorphous or in the form of a glass at room temperature (e.g. 25 degrees Celsius) so as to stabilise the entrapped protein as well as present the active in such a rapidly-soluble state. Preferably the composition exhibits a glass transition temperature of greater than about 25 degrees C., or about 30 degrees C., or about 40 degrees C., or about 50 degrees C., as measured by Differential Scanning calorimetry or modulated Differential Scanning calorimetry. The additive material may also be amorphous or in the form of a glass at room temperature (e.g. 25 degrees Celsius) so as to be in a rapidly-soluble state. Preferably the composition exhibits a glass transition temperature of greater than about 25 degrees C., or about 30 degrees C., or about 40 degrees C., or about 50 degrees C., as measured by Differential Scanning calorimetry or modulated Differential Scanning calorimetry. Such glassy compositions enable the composition to be stored at ambient or room temperature, e.g. 25 degrees C., for extended periods of time, for example greater than 3 months or greater than 6 months, without significant losses in activity. Significant losses are defined as losses in activity of greater than about 5 or 10 or 20 percent of original potency.

The additive material may also be in a crystalline or amorphous state but also be free-flowing, discrete and substantially anhydrous, with a residual moisture content preferably no greater than 5% w/w, most preferably no greater than 3% w/w.

Respective fibrinogen-containing and thrombin-containing soluble microparticles can be formulated and blended together, in stable, dry form to produce a fibrin sealant composition. This formulation can be subsequently activated, as desired, to give a fibrin sealant that is useful in wound therapy and surgical repair.

In an aspect of the present invention, the fibrin sealant powder composition is adapted to form a protective or preventative covering or bandage for minor abrasions, cuts, scrapes, scratches, burns, sunburns, ulcers and other skin injuries and irritations, such as bleeding during and post-surgery, and uncontrolled internal and external hemorrhage from heavy trauma and/or battlefield wounds.

In another embodiment the dry powder composition can be used as a topical hemostat to stop bleeding. In the present context, the time it takes to stop bleeding is called the time to hemostasis (TTH). If a pressure sheet is used, measurement of TTH typically starts when the pressure sheet is applied to the bleeding site and runs until bleeding stopped by visualization of the dressing and/or no bleeding through or around the dressing is observed.

In an aspect of the invention, the dry powder compositions according to the invention result in a TTH of about 10 minutes or less, about 5 minutes or less, or about 3 minutes or less.

Another object of the invention is the use of the dry powder compositions as described herein for the treatment of mild to moderate bleeding. Mild bleeds are those typically presenting with a blood flow of less than about 5 g/minute whereas moderate bleeds are often>20 g/minute, optionally with a TTH of less than 10 minutes.

Another object of the present invention is to provide a powder or fluid fibrin sealant composition adapted to form a seal on non-superficial tissues or to close open tissues exceeding minor abrasions, cuts, scrapes, scratches, burns, sunburns, ulcers and other skin injuries and irritations. Treatable wounds include: topical wounds; deeper wounds; surgical incisions; severe wounds; battlefield wounds and trauma; and emergency room excessive bleeding, among others. Accordingly, the various applications of the wound sealants include first aid and triage applications for surgical and medical procedures.

The powder composition of the invention may be applied directly to wounds, sutures, incisions and other openings where bleeding may occur. A wound includes damage to any tissue in a living organism. A biological tissue includes connective tissues, endothelial tissues, nervous tissues, muscle tissue and organs. Preferred biological tissues are selected from the group consisting of bone, skin, cartilage, spleen, muscle, lymphatic, renal, hepatic, blood vessels, lung, dura, bowel and digestive tissue. The tissue may be an internal (e.g. organ) or external tissue (e.g. eye, skin, etc.), and may be a hard tissue (e.g. bone) or a soft tissue (e.g. liver, spleen etc). The wound may have been caused by any agent, including infection, surgical intervention, burn or trauma. Trauma is defined as an injury caused by a physical force; examples include the consequences of motor vehicle accidents, gunshots and burns.

In another aspect of the invention, the dry powder fibrin sealant composition of the invention may be used for surgical interventions such as in the gastrointestinal system, e.g. the oesophagus, stomach, small intestine, large intestine, bowel, rectum, on parenchymal organs such as the liver, pancreas, spleen, lungs, kidney, adrenal glands, lymph and thyroid glands; surgical interventions in the ear, nose and throat area (ENT) including dental surgery, epistaxis, cardiovascular surgery, such as carotid endarterectomy, femoropopliteal bypass or coronary artery bypass grafting (CABG); aesthetic surgery, spinal surgery, neurological surgery, such as posterior lumbar interbody fusion, microdiscectomy or craniotomy; lymphatic, biliary, and cerebrospinal (CSF) fistulae, air leakages during thoracic and pulmonary surgery, thoracic surgery including surgery of the trachea, bronchi and lungs orthopaedic surgery, such as knee or hip replacement; gynaecological surgical procedures such as caesarian section, hysterectomy, fibroid surgery; vascular surgery, such as shunts; urological, bone (e.g. spongiosa resection), and emergency surgery. Particularly preferred surgical interventions include orthopaedic surgery, liver resection, soft tissue injury or surgery and vascular surgery.

The dry powder fibrin sealant composition of the invention demonstrated advantages over existing liquid systems comprising fibrinogen and thrombin, whereby these prior art products require reconstitution, have a short shelf life once reconstituted, often have to be delivered using a double-barrelled syringe due to their incompatibility in the liquid state. Furthermore, such liquid presentations are difficult to apply to awkward or complex surfaces of wounds and or organs and are also prone to run off and pool in cavities. The dry powder fibrin sealant composition and formulations described herein, overcome these drawbacks.

In a further aspect of the invention, the compositions of the invention are administered during or after surgery. The compositions of the invention may be administered to the wound or wounds of a subject, including human, mammal and other veterinary applications.

The invention further comprises a method for reducing bleeding at a hemorrhaging site by applying a composition comprising a hemostatically effective amount of the dry powder composition described herein.

In a further aspect of the invention, the powder composition is formulated either as a non-sterile or sterile preparation for single-delivery application to a wound site, or as a multi-use preparation. The preparation can be packaged and supplied in several preferential formulations including: dry powder, dry adhesive coating, aerosol, dry aerosol, pump spray, medical compress; film; coated plaster; medicated sponge or surgical patch (cf. Tachosil); hemostatic fleece (cf. Tachocomb); gauze; salve, semi-gel, gel, foam, paste, suspension, ointment, emulsion, moldable form, nasal plug, surgical dressing, wound packing, bandage, swab, catheter, fiber optic, syringe, pessary, suppository, or suspension in a liquid or non-aqueous liquid and the like. The formulations are applied topically to a wound site. Alternatively or in addition, the formulation can be introduced internally into the wound site in the case of, for example, deeper lacerations, arterial wounds, or during surgical procedures.

Another aspect of the invention provides a liquid hemostatic composition comprising the fibrin sealant powder as a suspension, for topical delivery on minor abrasions, cuts, scrapes, scratches, burns, sunburns, ulcers, internal venous bleeding, external venous bleeding, and surgical trauma.

Another preferred embodiment of the invention provides a liquid hemostatic composition for topical delivery on minor abrasions, cuts, scrapes, scratches, burns, sunburns, ulcers, internal venous bleeding, external venous bleeding, and surgical trauma, with said composition comprising the fibrin sealant powder composition in a non-aqueous liquid carrier for forming a thin-film barrier over the site of injury. The formulation may be easily applied to the wound site in variable quantities and will quickly stop bleeding.

The invention also comprises a process for preparing a viscous water soluble fibrin sealant paste, salve, ointment or suspension composition comprising the steps of: admixing the fibrin sealant powder composition of the invention and polyethylene glycol having a molecular weight range of from about 200 to 6000. Preferably blends of various molecular weights of PEG are used. Preferably, the PEG is a blend having an average molecular weight of in the range of 500 to 1,000, as a 1:1, or 1:2 or 1:3 or 1:5 or 1:9 blend of PEG 300 MW and 1500 MW. Use of lower grades of PEG will produce lighter, less viscous suspensions which can be packaged and delivered via a pump spray. Such suspensions may optionally include a surfactant or other suitable suspending agent, to prevent flocculation. Preparation and the formulation of such formats is known to those skilled in the art.

The paste, salve, ointment or suspension composition may also be used in conjunction with, for example, a gelatin sponge, gauze or collagen material by either coating such material as a substrate with the composition and applying it to the hemorrhaging site or first applying the compositon to a hemorrhaging site and placing the gelatin sponge, gauze or collagen on top of the composition and applying pressure thereto. The ointment, salve or paste of the present invention has a viscosity and potency which is high enough to permit its hemostatic effective use by a surgeon by dipping of a gloved finger into the paste and placing the paste over the bleeding site. The polyethylene glycol that is used in this aspect has an average molecular weight range of from about 500 to 1000 or more preferably about 900. Grades of polyethylene glycol can be combined with one another to produce unique properties. For example, PEG 1500, a solid at room temperature, while not soluble in liquid PEG 300 at room temperature may be combined together and heated above the melting point of the higher melting glycol (i.e. PEG 1500) to form a solution. For example, PEG 300 which is a liquid, is mixed with an equal weight of PEG 1500, a solid melting at 43 degrees C., 
and the two heated together at or above the melting point of PEG 1500 such that they liquify to a homogeneous solution, and when that solution is cooled to room temperature, it forms a smooth, soft paste. This paste is water soluble, and sufficiently yielding to spread readily on tissue or skin.

The invention further comprises a method for reducing bleeding at a hemorrhaging site by applying a paste composition comprising a hemostatic effective amount of the dry powder fibrin sealant composition of the invention in a base comprising polyethylene glycol to the hemorrhaging site of a subject. The paste may be applied in combination with a fibrous gauze material or by itself in paste form to the hemorrhaging site.

In a further embodiment of the invention, the fibrin sealant powder composition is admixed with a propellant and packaged in an aerosol container, optionally with a polymer such as PVP (see U.S. Pat. No. 4,752,466). This therefore provides a convenient way to deliver dry powdered thrombin directly to a wound, or directly onto a hemostat or support material as described herein. The amount of fibrin sealant powder composition used in each can could differ according to the potency desired, but typically might be on the order of magnitude of 0.5 to 1.0 gram. The propellant, in liquified form, then is filled into the aerosol container through the valve from a tank where it exists in liquified form. The amount of propellant used typically might be on the order of 10 grams. Other methods of filling an aerosol container are well known and may be used if desired. Inside the aerosol container, the synthetic polymer e.g. PVP completely dissolves in the propellant. The fibrin sealant powder composition does not dissolve, but exists in a very finely divided state, i.e., it is suspended in the propellant, where it exists as a finely divided milky suspension. When the valve is depressed to spray the material from the aerosol container, a mixture of fibrin sealant powder composition, propellant and optionally PVP is emitted. The fibrin sealant powder composition comes out as a dry white powder. The propellant evaporates quickly and disappears. Aerosol containers and components thereof designed for dispensing powder sprays are commercially available, and may be used in the present invention. In the "Handbook of Aerosol Technology" by Paul Sanders (Van Nostrand, Reinhold Company, N.Y. 1979, 2nd. ed. Chapter 21 entitled "Aerosol Suspensions) (Powders) gives helpful background information. Preferred propellants include those of the HFA series.

The aerosol package of the present invention should be prepared and handled in such manner that its contents will be sterile when sprayed. The use of bacterial filters and aseptic processing techniques results in a sterile product.

The aerosol of the present invention is designed to be stored at room temperature. In this form it is relatively stable for at least for periods of 6 months due to the glassy nature of the fibrin sealant powder composition.

In a most preferred embodiment of the invention, the fibrin sealant powder composition is applied using the powder delivery device of co-pending application WO 2010/070333, (Fibrospray™) herein incorporated by reference, for use in surgical interventions such as such as in the gastrointestinal system, e.g. the oesophagus, stomach, small intestine, large intestine, bowel, rectum, on parenchymal organs such as the liver, pancreas, spleen, lungs, kidney, adrenal glands, lymph and thyroid glands; surgical interventions in the ear, nose and throat area (ENT) including dental surgery, epistaxis, cardiovascular surgery, such as carotid endarterectomy, femoropopliteal bypass or coronary artery bypass grafting (CABG); aesthetic surgery, spinal surgery, neurological surgery, such as posterior lumbar interbody fusion, microdiscectomy or craniotomy; lymphatic, biliary, and cerebrospinal (CSF) fistulae, air leakages during thoracic and pulmonary surgery, thoracic surgery including surgery of the trachea, bronchi and lungs orthopaedic surgery, such as knee or hip replacement; gynaecological surgical procedures such as caesarian section, hysterectomy, fibroid surgery; vascular surgery, such as shunts; urological, bone (e.g. spongiosa resection), and emergency surgery. Particularly preferred surgical interventions include orthopaedic surgery, liver resection, soft tissue injury/surgery and vascular surgery.

In an preferred embodiment of the invention comprising a support material, such as a gauze, sponge, bandage and the like, it is proposed herein to spray or otherwise embed or apply the fibrin sealant powder composition in predetermined strengths such as for example: 20%, 40%, 60% or 80%, or any other preferred strengths, on the support and identify the strength of the fibrin sealant powder applied thereon. Methods of application of the fibrin sealant powder composition, or combinations of the fibrin sealant powder composition and other materials, into the treated support, are well known to those skilled in the art. The marking of the treated support could take the form of imprinting the percentage strength, e.g., 20%, 40% or 60%, on the surface of the treated support (on one or both sides) or just underneath one layer thereof. The percentage markings may be any other preferred figures, such as 25%, 50% and 75%, or even 1, 2, 3, 4, 5, as desired. After the marking is done, the treated support is subjected to sterilization as desired.

Such novel presentations of the dry powder fibrin sealant or topical hemostat, exhibit synergy and/or greater efficacy compared to the powder alone by encouraging clot formation at the interface of the wound and device where the dry powder fibrin sealant has been embedded and/or coated. Existing impregnated supports and sponges and the like allow the blood to seep into the structure before clotting occurs.

Other preferred methods of the invention are useful for sealing incisions, perforations, and/or fluid or gaseous leaks in biological tissues during a surgical procedure, and comprise contacting the tissue with an effective amount of a the fibrin sealant powder composition, thereby sealing the incision, perforation, or fluid or gaseous leak.

EXAMPLES

Example 1

Dry powder fibrin sealant was prepared, as described in co-pending application U.S. 61/122,063. In brief, Fibrinogen (ZLB, Marburg, Germany) and trehalose (Pfanstiehl, Waukegan, Ill., USA) hollow spherical particles were prepared, as described in application The concentration of fibrinogen in the particles is 12% (w/w).

Thrombin (SNBTS, Glasgow, Scotland) and trehalose were spray dried to obtain hollow particles.

Thrombin was present in a concentration of 1000 IU per gram of particles.

The particles were blended in a 1:1 ratio; the resulting powder has a 6% w/w concentration of fibrinogen and 500 IU/gram of powder. This blend is hereinafter referred to as Fibrocaps™.

In order to prepare the mixture of a further embodiment of the invention, the Fibrocaps powder above was further mixed 1:1 weight/weight with fluid absorbing particles (Sephadex G200 superfine, GE Healthcare, Uppsala, Sweden). Sephadex G200 superfine has a dry bead size of 10-40 μm. For clarity, the resulting powder consists of 3% w/w of fibrinogen, 250 IU/gram thrombin and 50% w/w of Sephadex G200 particles. This blend is named Sephadex-blended Fibrocaps™.

Efficacy Testing.

There is no universal animal model for testing efficacy of a topical hemostat available because trauma bleeding presents itself in different forms ranging from arterial injury with high pressure to massive oozing. Large animal models (pigs) are the only models representative for the human situation (Pusateri et al. (2003) J. Trauma 55(3), 518-526). In the animal models selected, the Sephadex-blended Fibrocaps™ product will be compared to other products that are on the market or in development and could potentially be used in trauma applications. To simulate a traumatic injury to the liver, inducing uncontrolled severe bleeding, a liver scallop injury was inflicted on the liver of a pig by cutting away with a pair of surgical scissors a 4×5 cm wide and 1.5-2 cm deep piece from the liver (n=2). None of the veins or arteries that were cut during this procedure were tied off and the animal had received a standard dose of heparin ~15 minutes before the injury was made.

Figure 1:
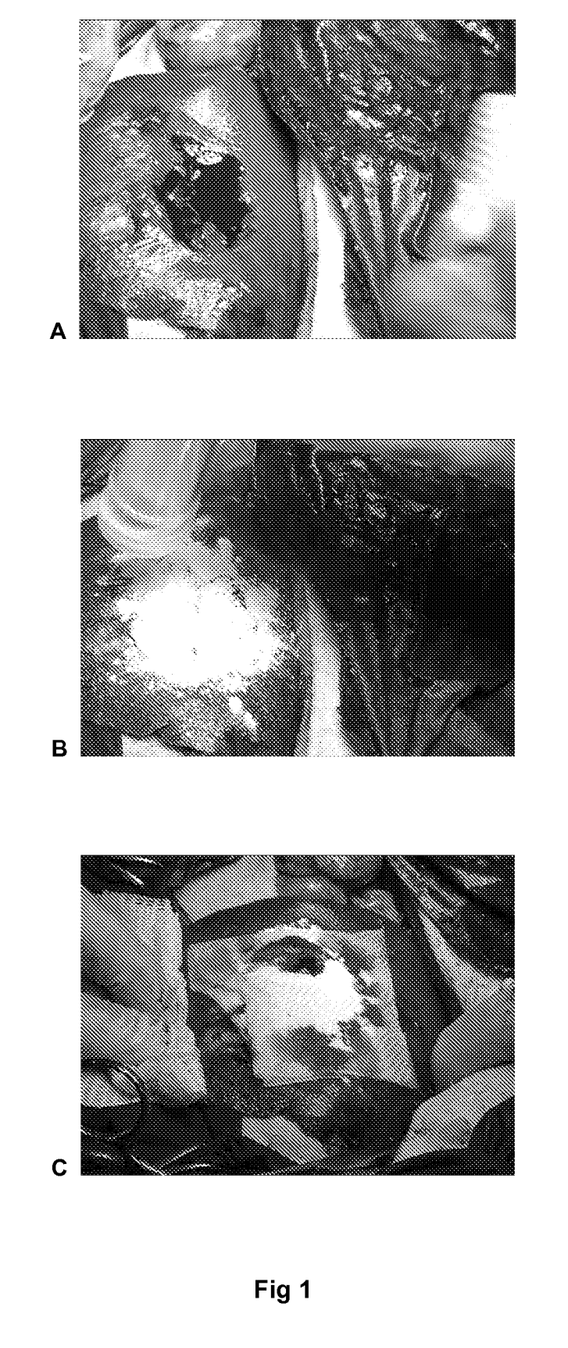

One injury was treated using the "standard" protocol in which 6 grams of Fibrocaps™ material was poured onto the wound, covered with piece of parafilm after which pressure was applied for 30 seconds. During removal of the parafilm a substantial portion of the powder was removed as well and an additional 1.5-2 grams was applied to the wound and pressure was applied with standard surgical gauze. The bleeding slowed down significantly within 2-3 minutes, but it took ~5 minutes to obtain complete hemostasis. The second scallop injury was treated with 6 grams of Sephadex-blended Fibrocaps™, having increased absorbing capacity, but only containing half of the amounts of fibrinogen and thrombin. The powder was then covered with a piece of biodegradable Vicryl sheet (Ethicon) and pressure was applied for 30 seconds using gauze. The gauze could be easily removed and the Vicryl was left on the wound to prevent disturbing the Fibrocaps™ plug. No bleeding was observed and complete hemostasis was achieved within 1-1.5 minutes (see also FIG. 1A-C). This time is referred to as time to hemostasis (TTH). Sephadex only was not able to stop severe bleedings in animals.

This experiment clearly demonstrates the advantage of Sephadex-blended Fibrocaps over Fibrocaps. Applying equal amounts of these powders on severe bleeding wounds results in complete hemostasis for Sephadex-blended Fibrocaps within 1.5 minutes, whereas Fibrocaps was able to stop the bleeding in 5 minutes, but only after adding additional powder. This is surprising, as Sephadex-blended Fibrocaps only contains half of the concentration of fibrinogen and thrombin as compared to Fibrocaps. Lower concentrations of fibrinogen and thrombin also implies a significant reduction in the cost of Sephadex-blended Fibrocaps as compared to Fibrocaps.

Example 2

In order to prepare a silicified composition with enhanced flow and hemostatic action, the Fibrocaps powder of Example 1 was further mixed with 0.5% w/w Aerosil200 Pharma (Evonik) in a Turbula low-shear blender for 10 minutes to produce a free-flowing powder.

Example 3

The Fibrocaps powder of Example 1 is placed in an open aerosol can or bottle, the valve stem and top are placed thereon and crimped into place. The amount fibrin sealant powder composition is approximately 1.5 grams. The propellant, in liquified form, then is filled into the aerosol container through the valve from a tank where it exists in liquified form. The aerosol is then applied to the wound by actuation of the valve to release the contents of the aerosol can, resulting in rapid hemostasis.

Example 4

The Fibrocaps powder of example 1 is admixed in a 1:1 ratio with PEG 200 and 0.5% Tween 80, to produce a light, liquid suspension and packaged in a bottle which is then be applied to a wound, resulting in rapid hemostasis.

Example 5

The Fibrocaps powder of example 1 is admixed in a 1:1 ratio with PEG 800 to produce a paste and packaged in a tube which is then be applied to a wound, resulting in rapid hemostasis.

Example 6

This Example outlines in detail several pharmacology studies that evaluate Fibrocaps (from Example 1) either alone or in combination with a variety of pressure sheets (e.g. gelatins USP, collagen, and oxidized cellulose) to promote hemostasis and reduce blood loss. The pharmacology models include wounds made in soft tissues (liver and spleen) and vascular models (AV graft). The models include mild bleeds (<5 g/min) to moderate bleeds (>20 g/min). Several of these studies also include gauze or other "mechanical" hemostatic controls as well as "active" topical hemostatic agents like human thrombins and FloSeal such that comparisons could be made to Fibrocaps.

Overall, these studies demonstrate that Fibrocaps is pharmacologically active and able to promote hemostasis as measured by reduced TTH and blood loss either alone or in combination with pressure sheets such as gelatins, collagens, and oxidized cellulose. In addition, Fibrocaps demonstrated comparable hemostatic activity to other marketed topical hemostatic agents. The recommended Fibrocaps dose per surface area is 1.5 g/100 cm$^2$.

Development of a Swine-Spleen Punch-Biopsy Model of Hemostasis

In this study, two animals were fasted prior to surgery and anesthetized as appropriate. Mean arterial pressure (MAP) was measured and recorded every 5 min via a catheter inserted into the femoral artery. Once blood pressure was stable for 20 min, a midline laparotomy was performed and the spleen was exteriorized. Untreated areas of the spleen were kept moist by coverage with lap sponges soaked in saline. Wounds were made using a 6 mm diameter biopsy punch 3 mm deep. The biopsy was removed by excision with scissors. Each wound was separated by enough space to allow for careful evaluation.

Fibrocaps powder from Example 1 was applied to each wound site as a dry powder (0.25 g) using the Fibrospray device described in WO 2010/070333. Avitene Ultrafoam (collagen) pre-wetted with saline, Surgicel materials, and a non-stick gauze pad (Dukal) were used to apply light manual pressure to allow the Fibrocaps to come into close contact with the wound bed. Control articles were applied using manufacturer's recommendations. Treated wounds had light, manual pressure applied initially for 1 min followed by a 30 second hemostasis evaluation. If bleeding continued, additional 30 second tamponade/30 second hemostasis evaluations were performed until hemostasis occurred or until trial testing reached 10 minutes and the treatment was recorded as a failure. Between 4 and 13 wounds were created for each treatment under evaluation. Time-to-hemostasis was measured from the time the pressure sheet was applied to the bleeding site until bleeding stopped by visualization of the dressing and/or no bleeding through or around the dressing was observed.

After an evaluation of different types/sizes of wounds on the first pig, it was observed that a 6 mm punch biopsy at a depth of 3 mm resulted in a consistent bleed rate across groups and animals. Using this approach, the model performed reliably, and the biopsy created wounds that yielded approximately 1.5 to 2 g/min of blood loss. No changes in MAP were noted after wounding or application of hemostatic treatments.

TABLE 1

Treatments Tested

| Treatment | Description |
| --- | --- |
| Surgicel Original | Oxidized cellulose sponge |
| Surgicel Nuknit | Thin, oxidized cellulose sponge |
| RECOTHROM/Gelfoam | Recombinant human thrombin + gelatin sponge |
| Fibrocaps + Avitene Ultrafoam | Fibrocaps + collagen sponge (pre-wetted with saline) |
| Fibrocaps + Dukal | Fibrocaps + non-adherent gauze pad |

Figure 2:
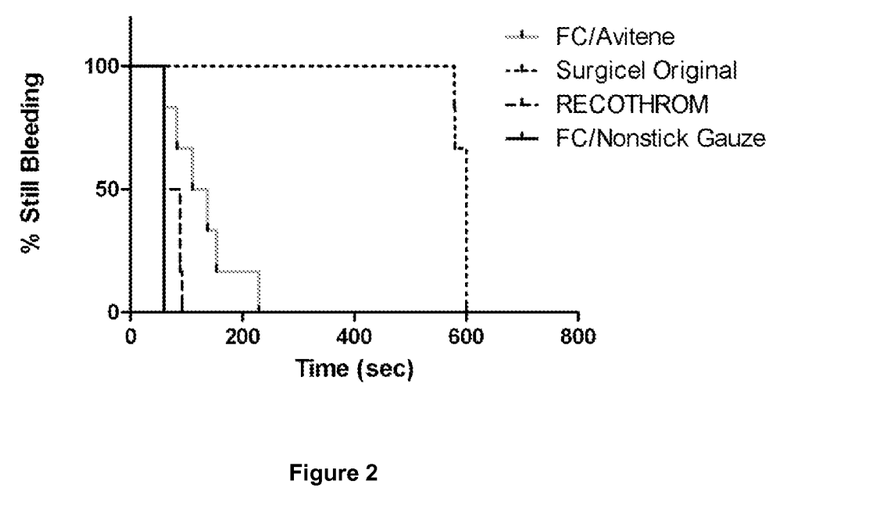
FIG. 2 Effect of various hemostatic agents on time to heamostatis (TTH) in Swine Punch-Biopsy Model.
Figure 3:
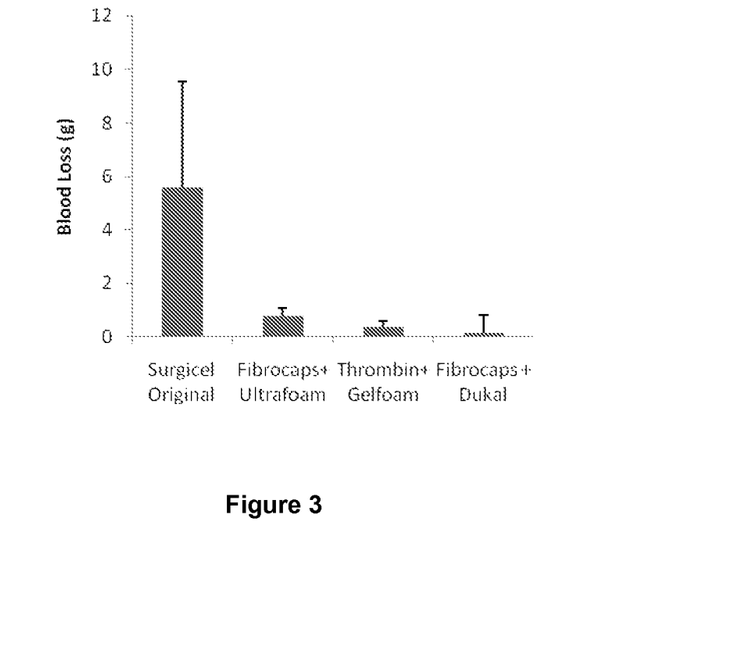
FIG. 3 Fibrocaps reduces blood loss compared to Surgicel.

Table 1 lists the treatments that were evaluated for their ability to shorten TTH and reduce blood loss in the second pig. Fibrocaps in combination with Avitene had a mean TTH=2.52 min, which was significantly shorter than Surgicel (Nuknit) (mean TTH=6.27 min) and Surgicel Original Hemostatic agents (mean TTH=9.88 min). Similar reductions in TTH were observed with Fibrocaps in combination with the non-adherent gauze pad, Dukal as compared to Surgicel Original Hemostatic agent. Fibrocaps took longer, but not significantly longer to achieve hemostasis when compared to recombinant human thrombin applied with Gelfoam (mean TTH=1.25 min). A Kaplan-Meier presentation of the data is shown in FIG. 2. In addition, all test and control sites achieved hemostasis with the exception of 4 of the 6 sites treated with Surgicel. These sites required the application of an additional hemostatic material following the 10 minute evaluation period and were recorded as hemostasis failures. The amount of blood lost during the experiment was greater in the Surgicel treatment group than the two groups treated with Fibrocaps or recombinant human thrombin (FIG. 3).

The results of this study demonstrated that creation of a 6×3 mm punch-biopsy wound in the swine spleen produced a consistent, mild hemorrhage.

These results demonstrate that Fibrocaps (used in combination with either Avitene Ultrafoam or Dukal Pad to apply pressure), consistently performed better than the Surgicel Original and Surgicel NuKnit (not shown) at achieving hemostasis and at controlling the volume of blood lost. The reduction in TTH with Fibrocaps plus either Avitene Ultrafoam or the Dukal Pad was similar to that of the thrombin plus Gelfoam.

Fibrocaps Pharmacology in a Swine Spleen Punch-Biopsy

These two studies extended the use of the swine spleen, punch-biopsy model using the 6×3 mm punch biopsy and evaluating the effects of various hemostatic agents, alone or in combination, on TTH and blood loss measurements as previously described (Table 2).

TABLE 2

Treatment Groups in the Swine Spleen Punch-Biopsy Model

| Treatment Groups[1] | Description |
| --- | --- |
| Gauze | Cotton gauze pad |
| Fibrocaps + Surgifoam | Fibrocaps + gelatin sponge (USP) |
| Surgifoam | Gelatin Sponge |
| Fibrocaps + Gelfoam | Fibrocaps + gelatin sponge (USP) |
| Gelfoam | Gelatin Sponge |
| Gauze | Cotton gauze pad |
| Fibrocaps + Surgicel | Fibrocaps + oxidized cellulose |
| Surgicel | Oxidized cellulose |

[1]Wounds were created according to a randomization schedule. 7-10 wounds were created/spleen and each group had n = 6 wounds/treatment.

Figure 4:
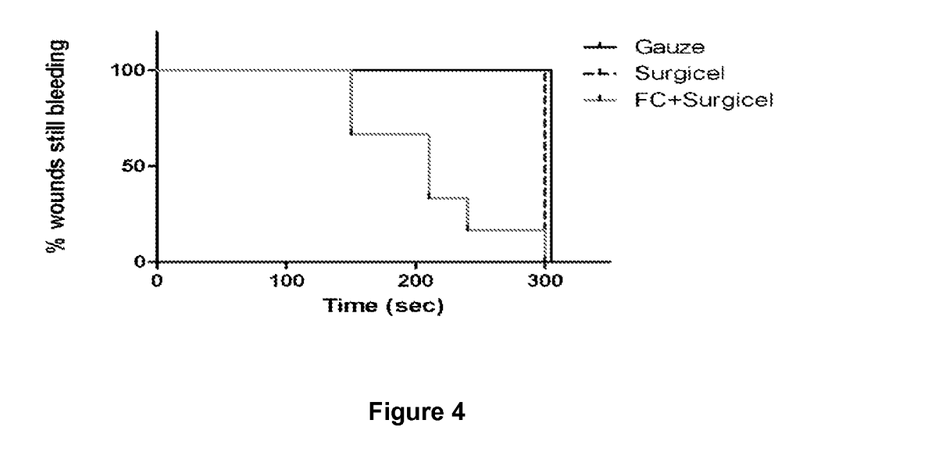
FIG. 4 Fibrocaps+Surgicel reduces TTH Compared to Surgicel alone in a Swine-Spleen, Punch-Biopsy Model.
Figure 5:
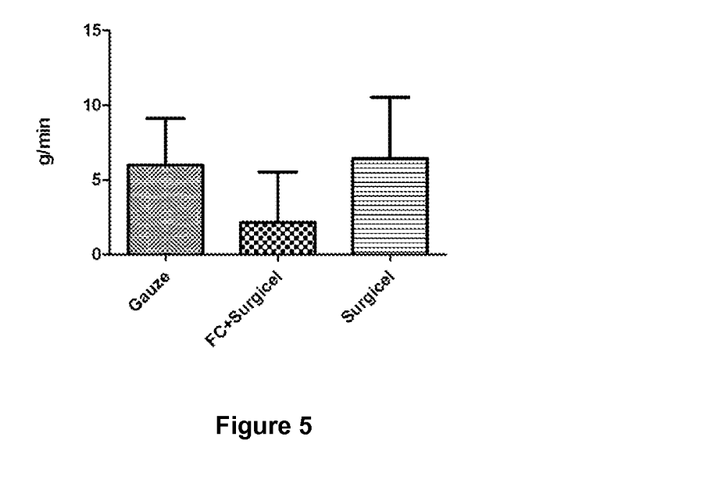
FIG. 5 Fibrocaps+Surgicel reduces blood loss compared to Surgicel Alone in a Swine Spleen, Punch-Biopsy Model.

As in the previous study above, the mild bleed rates were similar across treatment groups. With low bleeding rates of approximately 2 g/min, gelatin sponges pre-wetted with saline were able to control the bleeding and promote hemostasis within approximately 2.5 min. Therefore, no significant improvements in TTH could be made with the addition of Fibrocaps. This result was not unexpected considering that gelatin sponges have US and EU market authorization for use in the control of mild surgical bleeding. As in the previous study, Surgicel was unable to control bleeding in this study. However, Fibrocaps in combination with Surgicel was able to promote rapid hemostasis resulting in reductions in TTH as compared to Surgicel alone (FIG. 4). Similar reductions were also observed for blood loss (FIG. 5). As expected, both gelatin sponges (Gelfoam and Surgifoam), alone or with Fibrocaps, were able to promote hemostasis and reduce blood loss when used alone in this swine spleen, punch-biopsy model. Surgicel alone was ineffective, like gauze. However, when Fibrocaps was added to Surgicel hemostasis was achieved and blood loss was reduced. These results show that Fibrocaps can be beneficial even in mild bleeding situations when used with other approved hemostatic agents.

Effects of Fibrocaps in a Rabbit Liver Resection Model

In this study, the liver of eight animals was exteriorized and wounds were made by resecting a nearly circular portion of the liver approximately 1 cm in diameter. In most cases, 4 lesions were created per animal across the various liver lobes. The resected liver portion from each wound was weighed to evaluate model consistency. Blood was collected from the wound for 30 seconds to determine a bleed rate to evaluate consistency in bleeding from wound to wound. Treatments were then applied to the sites in a randomized fashion (Table 3).

TABLE 3

Treatment Groups in a Rabbit Liver Resection Model

| Group | Treatment (n = 6) | Description |
| --- | --- | --- |
| 1 | Avitene | Collagen Sponge |
| 2 | Fibrocaps + Avitene | Fibrocaps + Collagen |
| 3 | Surgicel Original Hemostatic Agent | Oxidized cellulose |

Figure 6:
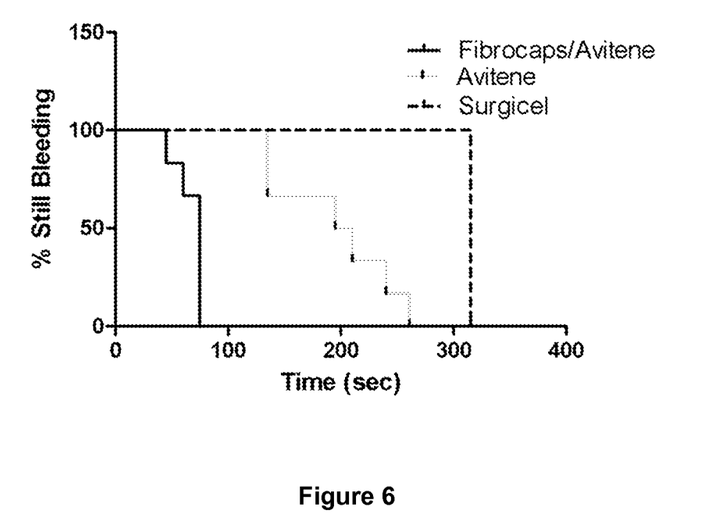
FIG. 6 Fibrocaps+Avitene reduces TTH compared to Avitene or Surgicel alone.
Figure 7:
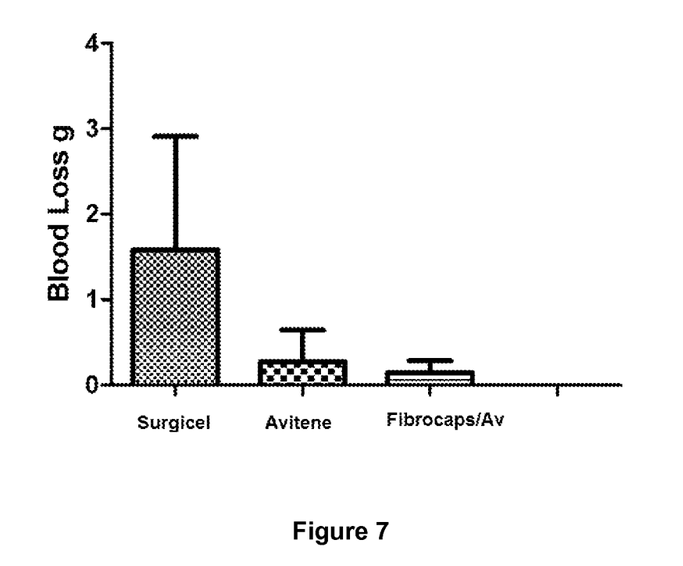
FIG. 7 Fibrocaps and Avitene reduces blood loss in a Rabbit Liver Model.

Fibrocaps was applied with the Fibrospray device to cover the entire wound. The device was loaded with 0.25 g of Fibrocaps powder for each wound. The device was evacuated onto the wound and light manual pressure with a collagen fleece was applied to bring the Fibrocaps powder in contact with the wound bed. A dry gauze dressing was applied over the treatment site to collect any blood seeping through the treatment and to measure blood loss. The bleeding rates and weights of excised fragments from the livers were similar across the treatment groups evaluated with the exception of the Surgicel group, which had a lower bleeding rate (data not shown). As shown in FIG. 6, Fibrocaps with Avitene was able to reduce TTH as compared to Avitene alone and to Surgicel alone. Surgicel achieved hemostasis in only 3 of 6 wounds at the last observation time (t=300 sec). Blood loss was also measured in each of the treatment groups. As shown in FIG. 7, both Fibrocaps in combination with Avitene, and Avitene alone were able to reduce blood loss compared to Surgicel. Fibrocaps was effective in reducing TTH as compared to Avitene or Surgicel alone, and demonstrated an additive hemostatic effect beyond the tamponade benefit of Avitene when used in combination.

Pharmacology of Fibrocaps+Gelatin Sponge in a Swine Liver Punch-Biopsy Model

This model has the advantage of yielding bleed rates that are typically>5-times higher than those observed in the swine spleen model and rabbit liver model. This more robust bleeding model allowed for an evaluation of TTH with Fibrocaps under "moderate" bleeding conditions. Another objective was to evaluate a more refined version of the Fibrospray device. The swine liver bleeding model has been used extensively to study hemostasis of Fibrocaps as well as other hemostatic agents.

The treatment groups are presented in Table 4 Briefly, under sterile conditions, liver lobes were isolated and non-overlapping biopsies were created with a 10 mm punch biopsy on each lobe, which were completely excised using scissors and forceps to a depth of approximately 4 mm. Blood was collected for a 1 minute period, to determine the base line bleeding rate. Normal saline soaked gauze was used to maintain the liver in a moist environment.

TABLE 4

Treatment Groups for Swine Liver Punch-Biopsy Model

| Group | Treatment | Description |
|---|---|---|
| 1 | Fibrocaps + Spongostan[1] | Fibrocaps + Gelatin sponge USP |
| 2 | Human Thrombin + Spongostan[2] | Human plasma derived thrombin + Gelatin sponges USP |
| 3 | Spongostan + saline[3] | Gelatin sponge USP + saline |

Figure 8:
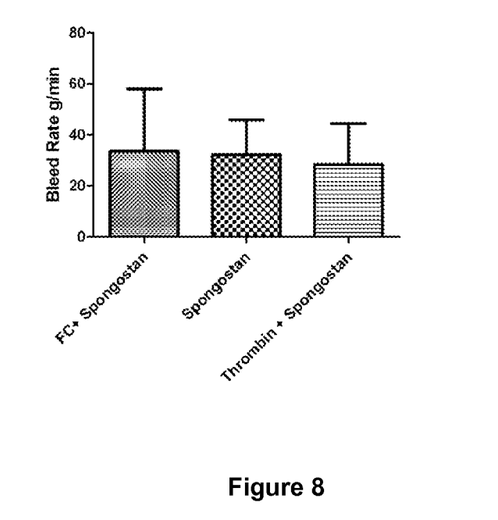
FIG. 8 Similar Bleed Rates in Swine Liver Punch Biopsy Model.
Figure 9:
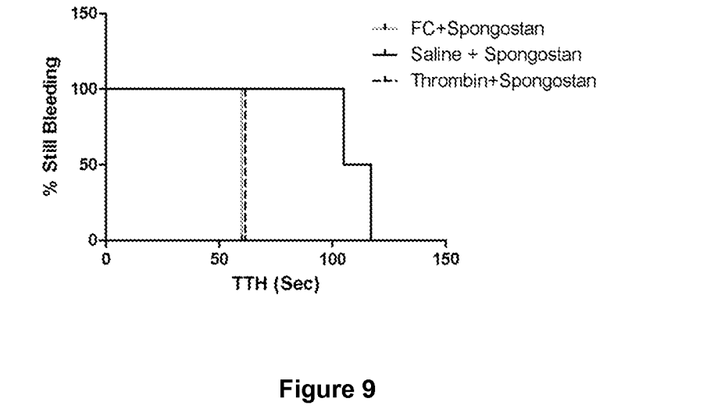
FIG. 9 Fibrocaps or Thrombin plus Spongostan shortens TTH compared to Spongostan alone.

[1]N = 4 wounds/treatment. Spongostan is the same as Surgifoam.
[2]N = 4 wounds/treatment. Human thrombin was reconstituted to 1000 IU/mL in saline according to the manufacturer's instructions
[3]N = 2 wounds/treatment The bleeding rates were considered moderate and similar between treatment groups (FIG. 8). As expected, the observed rates were approximately 5- to 10-times higher on average than those observed in the swine spleen or rabbit liver models. As shown in FIG. 9, Fibrocaps in combination with Spongostan reduced TTH as compared to Spongostan alone. In addition, Fibrocaps in combination with Spongostan was able to reduce TTH similarly to human plasma derived thrombin in combination with Spongostan. These data demonstrate that Fibrocaps in combination with a gelatin pressure sheet was able to promote hemostasis similar to that of human plasma thrombin in a more robust model of bleeding.

Fibrocaps in a Swine Liver Surgical Biopsy Model

In this study, 22 pigs were fasted overnight prior to surgery and were anesthetized according to the internal standard procedure. A midline laparotomy was performed to access the liver. Using a scalpel, four subcapsular standardized lesions (10 mm by 10 mm with a depth of approximately 3 mm) on the diaphragm side of the left medial (site 1 and 2) and lateral (site 3 and 4) lobes of the liver were created. Stitches with non-resorbable sutures were used to locate the lesions for histological determination. Pre-treatment blood loss was measured by applying a gauze for one minute (the gauze was weighed before and after application to evaluate the blood loss of each lesion). Subsequently each lesion was treated with one of the hemostatic treatments according to a pre-determined randomization schedule, whereby each of the four treatments in Table 6 were applied to one of four surgical bleeding wounds on each liver.

TABLE 5

Treatment Groups for Swine Liver Surgical Biopsy Model Study

| Group | Treatment | Description |
|---|---|---|
| Control 1 | Avitene Ultrafoam | Collagen Sponge |
| Control 2 | Gelfoam | Gelatin Sponge USP |
| Treatment 1 | Fibrocaps + Avitene | Fibrocaps 0.5 g + Avitene |
| Treatment 2 | Fibrocaps + Gelfoam | Fibrocaps 0.5 g + Gelfoam |

In this study, for Treatments 1 and 2, Fibrocaps powder was pressed using moderate manual pressure onto the wound for 30 seconds using a 40×30 mm piece of Avitene or Gelfoam, respectively. For the Control groups, the same time and pressure was used in the absence of Fibrocaps. If the bleeding did not stop within a minute, pressure was applied again for 30 seconds. This was repeated at 1-minute intervals until hemostasis was achieved. Hemostasis was considered achieved if no bleeding was observed for 3 minutes after pressure release. Treatments and controls were left in place.

In addition to TTH and blood loss, the following safety assessments were recorded for each treatment: local swelling, adhesion to the wound site, secondary detachment, color and any other relevant findings. The pre-treatment blood loss was similar across the groups, (see Table) demonstrating that the wounds presented similar bleeding challenges. All four treatments (n=22 per treatment) were able to achieve hemostasis in <1 min (Table 6 and 7). The hemostatic performance of the Fibrocaps in combination with Avitene versus Avitene alone was not statistically significantly different. The hemostatic performance of the Fibrocaps in combination with Gelfoam resulted in a statistically faster TTH when compared to Gelfoam alone (p=0.004).

TABLE 6

Pre-Treatment Blood Loss and TTH

| Parameter | Avitene | Fibrocaps + Avitene | P Value |
|---|---|---|---|
| Blood Loss (g) | 5.8 | 5.4 | P = 0.656 |
| TTH (min) | 0.6 ± 0.2 | 0.5 ± 0.1 | P > 0.05 | n = 22 per treatment group

TABLE 7

Pre-Treatment Blood Loss and TTH

| Parameter | Gelfoam | Fibrocaps + Gelfoam | P Value |
|---|---|---|---|
| Blood Loss (g) | 4.5 | 4.8 | P = 0.656 |
| TTH (min) | 0.7 ± 0.4 | 0.5 ± 0 | P = 0.004 | n = 22 per treatment group

Under the conditions of the study, the secondary characteristics such as local swelling/thickness, adhesion and secondary detachment to the wound site were considered equivalent (data not shown). Fibrocaps, in combination with collagen or gelatin sponges, was shown to be safe, well-tolerated and effective in a rabbit liver surgical biopsy model.

Pilot Study of Fibrocaps in a Sheep PTFE Vascular Graft Model

In this pilot study, one sheep was fasted and water withheld overnight, and anesthetized using isoflurane inhalation anesthesia (1-3.5% isoflurane in oxygen). Vital signs were monitored during anesthesia using a non-invasive cuff monitor and included heart rate, oxygen saturation, and respiratory rate (controlled by the ventilator when in use). Both the left and right carotid arteries and left and right external jugular veins were isolated using blunt and sharp dissection. Heparin (150 U/kg, IV) was administered five minutes prior to arterial clamping. The artery was then occluded with silicone vascular occlusion loop and a PTFE graft was anastomosed with running polypropylene sutures (5-0 Mersilene). For the first two anastomoses (left carotid to right jugular) the Fibrocaps (0.25 g/anastomotic end) was sprayed directly onto the arterial and venous anastomosis sites using the Fibrospray device in a single application and the occlusion loops were removed. There was slight bleeding at the arterial site that was completely stopped by a second application of 0.25 g Fibrocaps in less than two minutes. The right carotid-left jugular graft had blood flow established prior to Fibrocaps application. Two applications of 0.25 g each reduced the blood flow significantly, but did not stop it completely until a saline-wetted Gelfoam sponge was applied on top of the Fibrocaps. In total 4 sites were treated as outlined in the Table 8.

TABLE 8

Study Design for Sheep AV Graft Model

| Anastomotic Site | Application Prior to Removal of Occlusion Loops (Y/N) | Treatment |
|---|---|---|
| 1-arterial | N | Fibrocaps (2 × 0.25 g) |
| 2-venous | N | Fibrocaps (2 × 0.25 g) |
| 3-arterial | Y | Fibrocaps (2 × 0.25 g) |
| 4-venous | Y | Fibrocaps (2 × 0.25 g) |

The seal provided by application of Fibrocaps was relatively strong as demonstrated when the surgeon lifted one end of the graft to pull gently on the anastomosis site and no re-bleeding occurred.

In addition to the anastomotic sites, three large needle holes were made with a 25-gauge needle into the first ePTFE graft after hemostasis had been achieved at the anastomotic sites on both ends of the graft. Two successive applications of Fibrocaps failed to stop the bleeding from these puncture sites in the absence of any pressure sheet. Upon the subsequent application of saline-wetted Gelfoam on top of the Fibrocaps, the bleeding immediately stopped. A single, needle puncture hole was made in the second graft and bleeding was stopped with a single application of Fibrocaps.

The vascular surgeon found no problems with using the spray device to apply the Fibrocaps to the anastomotic sites even with a tubular wound area that was partially obscured by the vessel itself.

Fibrocaps was able to adhere to the synthetic ePTFE graft and stop bleeding in the sheep vascular graft model for moderate bleeding in under 2 minutes at the arterial and venous anastomotic sites (n=4) regardless of whether the occlusion loops were removed before or after Fibrocaps application.

The invention claimed is:

1. A pharmaceutical dry powder composition comprising a mixture of spray-dried first microparticles that comprise human fibrinogen, and spray-dried second microparticles that comprise human thrombin, for use as a haemostat in the topical treatment of a mild or moderate bleeding wound with a time to hemostasis of less than 5 minutes, wherein the mixture has an X50 value between 5 and 50 microns, and wherein the wound is selected from minor abrasions, cuts, scrapes, scratches, burns, sunburns, ulcers, internal venous bleeding, external venous bleeding, and surgical interventions selected from those involving gastrointestinal system, on parenchymal organs; surgical interventions in the ear, nose and throat area (ENT) cardiovascular surgery, aesthetic surgery, spinal surgery, neurological surgery; lymphatic biliary, and cerebrospinal (CSF) fistulae air leakages during thoracic and pulmonary surgery, thoracic surgery, orthopaedic surgery; gynaecological surgical procedures; vascular surgery and emergency surgery.

2. A pharmaceutical dry powder composition according to claim 1 wherein the surgical intervention is selected from orthopaedic surgery, liver resection, soft tissue injury or surgery and vascular surgery.

3. A pharmaceutical dry powder composition according to claim 1 wherein the use is characterized by the topical application to a wound during or after surgery.

4. A pharmaceutical dry powder composition as claimed in claim 1, wherein said first microparticles contain 0.5 to 20% w/w fibrinogen.

5. A pharmaceutical dry powder composition as claimed in-claim 1, wherein said second microparticles comprise 25 to 1000 IU/g thrombin.

6. A pharmaceutical dry powder composition as claimed in claim 1, which further comprises 0.01 to 95% w/w of an additive material.

7. A pharmaceutical dry powder composition as claimed in claim 1, wherein the fibrinogen and/or thrombin are recombinant.

8. A pharmaceutical dry powder composition according to claim 7 wherein the recombinant fibrinogen is HMW fib or alpha-extended fib.

9. A method of treating a wound, comprising administering to the wound a pharmaceutical dry powder composition comprising a mixture of spray-dried first microparticles that comprise human fibrinogen, and spray-dried second microparticles that comprise human thrombin, for use as a haemostat in the topical treatment of a mild or moderate bleeding wound with a time to hemostasis of less than 5 minutes, wherein the mixture has an X50 value between 5 and 50 microns, and wherein the wound is selected from minor abrasions, cuts, scrapes, scratches, burns, sunburns, ulcers, internal venous bleeding, external venous bleeding, and surgical interventions selected from those involving gastrointestinal system, on parenchymal organs; surgical interventions in the ear, nose and throat area (ENT) cardiovascular surgery, aesthetic surgery, spinal surgery, neurological surgery lymphatic biliary, and cerebrospinal (CSF) fistulae air leakages during thoracic and pulmonary surgery, thoracic surgery, orthopaedic surgery; gynecological surgical procedures, vascular surgery and emergency surgery.

10. A method according to claim 9, wherein said treatment results in a time to hemostasis of 3 minutes or less following administration.

11. A formulation comprising the pharmaceutical dry powder composition according to claim 1, wherein the formulation is a dry adhesive coating, aerosol, dry aerosol, pump spray, medical compress; film; coated plaster; medicated sponge or surgical patch; hemostatic fleece; gauze; salve, semi-gel, gel, foam, paste, suspension, ointment, emulsion, mouldable form, nasal plug, surgical dressing, wound packing, bandage, swab, catheter, fiber optic, syringe, pessary, suppository, or suspension in a liquid or non-aqueous liquid.

12. A pharmaceutical dry powder composition as claimed in claim 1, wherein the mixture has an X50 value between 10 and 20 microns.

13. A method of treating a wound according to claim 9, wherein the mixture has an X50 value between 10 and 20 microns.

14. The method of treating a wound according to claim 9, wherein the pharmaceutical dry powder composition is in a formulation selected from a dry adhesive coating, aerosol, dry aerosol, pump spray, medical compress, film, coated plaster, medicated sponge or surgical patch, hemostatic fleece, gauze, salve, semi-gel, gel, foam, paste, suspension, ointment, emulsion, mouldable form, nasal plug, surgical dressing, wound packing, bandage, swab, catheter, fiber optic, syringe, pessary, suppository, and a suspension in a liquid or non-aqueous liquid.

15. The method of treating a wound according to claim 14, wherein the mixture has an X50 value between 10 and 20 microns.

* * * * *